(12) United States Patent
Bathe et al.

(10) Patent No.: US 7,524,657 B2
(45) Date of Patent: Apr. 28, 2009

(54) ALLELES OF THE SIGA GENE FROM CORYNEFORM BACTERIA

(75) Inventors: Brigitte Bathe, Salzkotten (DE); Stephan Hans, Osnabrück (DE); Caroline Reynen, Steinhagen (DE); Walter Pfefferle, Halle (DE)

(73) Assignee: Evonik Degussa GmbH, Essen (DE)

( * ) Notice: Subject to any disclaimer, the term of this patent is extended or adjusted under 35 U.S.C. 154(b) by 492 days.

(21) Appl. No.: 10/498,887

(22) PCT Filed: Oct. 16, 2002

(86) PCT No.: PCT/EP02/11561

§ 371 (c)(1), (2), (4) Date: Jun. 16, 2004

(87) PCT Pub. No.: WO03/054179

PCT Pub. Date: Jul. 3, 2003

(65) Prior Publication Data

US 2005/0043526 A1 Feb. 24, 2005

(30) Foreign Application Priority Data

Dec. 20, 2001 (DE) ................................ 101 62 729

(51) Int. Cl.
- C12P 21/06 (2006.01)
- C12P 13/04 (2006.01)
- C12N 1/20 (2006.01)
- C12N 15/00 (2006.01)
- C07K 14/00 (2006.01)
- C07K 17/00 (2006.01)
- C07H 21/04 (2006.01)
- C07H 21/02 (2006.01)

(52) U.S. Cl. .................... 435/115; 435/69.1; 435/106; 435/252.3; 435/252.32; 435/320.1; 530/350; 536/23.1; 536/23.7

(58) Field of Classification Search ........................ None
See application file for complete search history.

(56) References Cited

U.S. PATENT DOCUMENTS 5,179,010 A * 1/1993 Yoshihara et al. ........... 435/115
2002/0197605 A1* 12/2002 Nakagawa et al. ............. 435/6

FOREIGN PATENT DOCUMENTS

EP 1 108 790 A3 6/2001
WO WO 01 66573 A 9/2001

OTHER PUBLICATIONS

Blackburn et al. Nature Structural Biology vol. 7 No. 10 Oct. 2000 p. 847-850.*
Collins et al. Proc. Natl. Acd. Sci. vol. 92 p. 8036-8040, Aug. 1995.*
Rodwell et al in Harper's Biochemistry 23rd edition, chapter 4, p. 27-28.*
Stenesh, J. Dictionary of Biochemistry and Molecular Biology (2nd Edition). (pp. 97). John Wiley & Sons. Online version available at: http://www.knovel.com/knovel2/Toc.jsp?BookID=968 &VerticalID=0.*
Brevet et al.Molec. Gen. Genet. 128,223-231 (1974).*
Halgasova Nora et al., "Cloning and Transcriptional Characterization of Two Sigma Factor Genes, SigA and SigB, from *Brevibacterium Flavum*," Current Microbiology, vol. 43, No. 4, Oct. 2001, pp. 249-254, XP002227863 ISSN: 0343-8651.
Gomez Manuel et al, "SigA Is an Essential Gene in Mycobacterium Smegmatis," Molecular Microbiology, vol. 29, No. 2, Jul. 1998, pp. 617-628, XP002227864, ISSN: 0950-382X.
Oguiza J A et al., "Multiple Sigma Factor Genes in Brevibacterium Lactofermentum: Characterization of sigA and sigB," Journal of Bacteriology, Washington, DC, US, vol.178, No. 2, Jan. 1996, pp. 550-553, XP002183859, ISSN: 0021-9193.
International Search Report dated May 2, 2003.

* cited by examiner

*Primary Examiner*—Robert B Mondesi
*Assistant Examiner*—Oluwatosin Ogunbiyi
(74) *Attorney, Agent, or Firm*—Michael A. Sanzo; Law Office of Michael A. Sanzo, LLC

(57) ABSTRACT

The invention relates to alleles of the sigA gene from coryneform bacteria which code for sigma factors A and a process for the fermentative preparation of L-lysine using bacteria which contain these alleles.

17 Claims, 1 Drawing Sheet

Figure 1: Plasmid pK18mobsacB_sigA_A414V
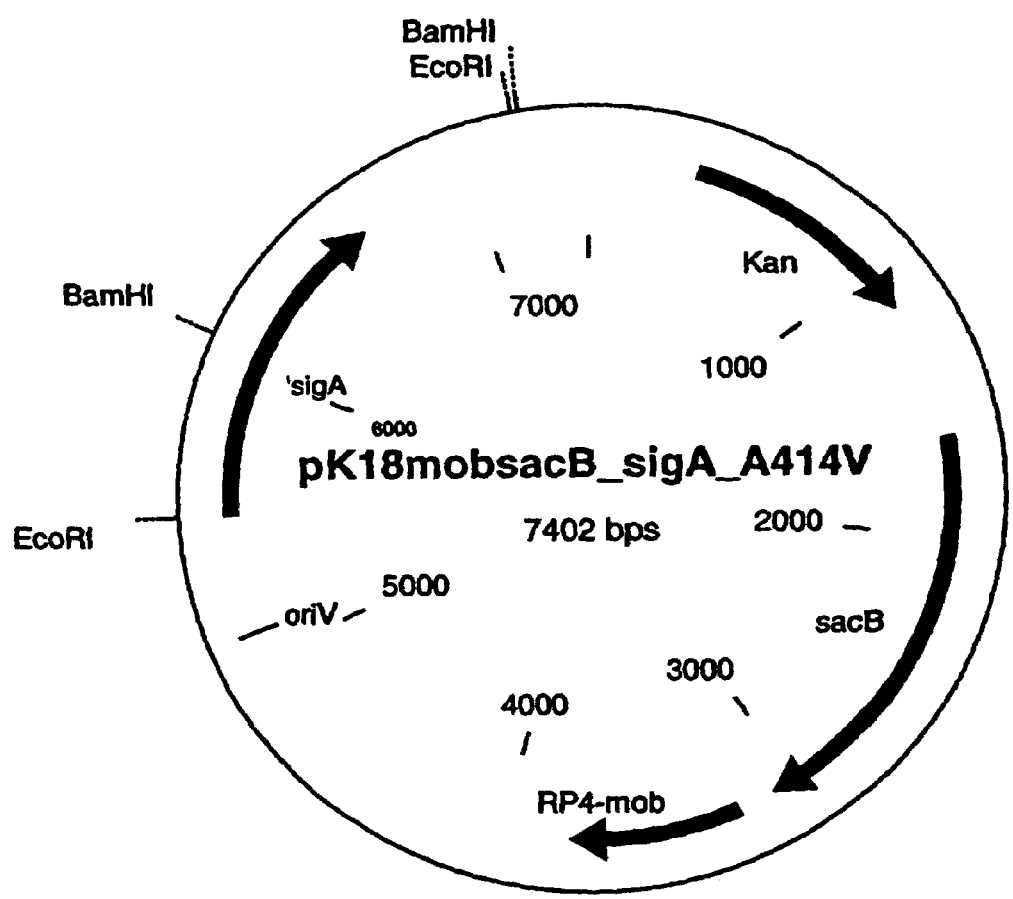

SEQUENCE LISTING

<160> NUMBER OF SEQ ID NOS: 12

<210> SEQ ID NO 1
<211> LENGTH: 1497
<212> TYPE: DNA
<213> ORGANISM: Corynebacterium glutamicum
<220> FEATURE:
<221> NAME/KEY: CDS
<222> LOCATION: (1)..(1494)
<223> OTHER INFORMATION: sigA wild-type gene

<400> SEQUENCE: 1

```
gtg gag agc agc atg gta gaa aac aac gta gca aaa aag acg gtc gct      48
Met Glu Ser Ser Met Val Glu Asn Asn Val Ala Lys Lys Thr Val Ala
1               5                   10                  15 aaa aag acc gca cgc aag acc gca cgc aaa gca gcc ccg cgc gtg gca      96
Lys Lys Thr Ala Arg Lys Thr Ala Arg Lys Ala Ala Pro Arg Val Ala
            20                  25                  30 acc cca ttg gga gtc gca tct gag tct ccc att tcg gcc acc cct gcg     144
Thr Pro Leu Gly Val Ala Ser Glu Ser Pro Ile Ser Ala Thr Pro Ala
        35                  40                  45 cgc agc atc gat gga acc tca acc cct gtt gaa gct gct gac acc ata     192
Arg Ser Ile Asp Gly Thr Ser Thr Pro Val Glu Ala Ala Asp Thr Ile
    50                  55                  60 gag acc acc gcc cct gca gcg aag gct cct gcg gcc aag gct ccc gct     240
Glu Thr Thr Ala Pro Ala Ala Lys Ala Pro Ala Ala Lys Ala Pro Ala
65                  70                  75                  80 aaa aag gtt gcc aag aag aca gct cgc aag gca cct gcg aaa aag act     288
Lys Lys Val Ala Lys Lys Thr Ala Arg Lys Ala Pro Ala Lys Lys Thr
                85                  90                  95 gtc gcc aag aaa gcc aca acc gcc aag gct gca cct gca act gcc aag     336
Val Ala Lys Lys Ala Thr Thr Ala Lys Ala Ala Pro Ala Thr Ala Lys
            100                 105                 110 gac gaa aac gca cct gtt gat gac gac gag gag aac ctc gct cag gat     384
Asp Glu Asn Ala Pro Val Asp Asp Asp Glu Glu Asn Leu Ala Gln Asp
        115                 120                 125 gaa cag gac ttc gac ggc gat gac ttc gta gac ggc atc gaa gac gaa     432
Glu Gln Asp Phe Asp Gly Asp Asp Phe Val Asp Gly Ile Glu Asp Glu
    130                 135                 140 gaa gat gaa gac ggc gtc gaa gcc ctc ggt gaa gaa agc gaa gac gac     480
Glu Asp Glu Asp Gly Val Glu Ala Leu Gly Glu Glu Ser Glu Asp Asp
145                 150                 155                 160 gaa gag gac ggc tca tcc gtt tgg gat gaa gac gaa tcc gca acc ctg     528
Glu Glu Asp Gly Ser Ser Val Trp Asp Glu Asp Glu Ser Ala Thr Leu
                165                 170                 175 cgt cag gca cgt aaa gat gcc gag ctc acc gct tcc gcc gac tct gtt     576
Arg Gln Ala Arg Lys Asp Ala Glu Leu Thr Ala Ser Ala Asp Ser Val
            180                 185                 190 cgc gct tac ctg aag caa atc ggt aaa gtt gcc ctg ctg aac gct gaa     624
Arg Ala Tyr Leu Lys Gln Ile Gly Lys Val Ala Leu Leu Asn Ala Glu
        195                 200                 205 cag gaa gtc tcc ctg gca aag cgc atc gaa gca ggc ctt tac gcc acc     672
Gln Glu Val Ser Leu Ala Lys Arg Ile Glu Ala Gly Leu Tyr Ala Thr
    210                 215                 220 cac cgc atg gag gaa atg gaa gaa gct ttc gca gcc ggt gac aag gac     720
His Arg Met Glu Glu Met Glu Glu Ala Phe Ala Ala Gly Asp Lys Asp
225                 230                 235                 240 gcg aaa ctc acc cca gcc gtc aag cgt gac ctc gcc atc gct cgt     768
Ala Lys Leu Thr Pro Ala Val Lys Arg Asp Leu Arg Ala Ile Ala Arg
                245                 250                 255
```

```
gac ggc cgc aag gcg aaa aac cac ctc ctg gaa gcc aac ctt cgt ctg         816
Asp Gly Arg Lys Ala Lys Asn His Leu Leu Glu Ala Asn Leu Arg Leu
            260                 265                 270 gtt gtc tcc ctg gca aag cgc tac acc ggc cgt ggc atg gca ttc ctg         864
Val Val Ser Leu Ala Lys Arg Tyr Thr Gly Arg Gly Met Ala Phe Leu
            275                 280                 285 gac ctc atc cag gaa ggc aac ctc ggt ctg att cgt gcc gta gag aag         912
Asp Leu Ile Gln Glu Gly Asn Leu Gly Leu Ile Arg Ala Val Glu Lys
            290                 295                 300 ttc gac tac tcc aag ggc tac aag ttc tcc acc tac gca acc tgg tgg         960
Phe Asp Tyr Ser Lys Gly Tyr Lys Phe Ser Thr Tyr Ala Thr Trp Trp
305                 310                 315                 320 atc cgt cag gca atc acc cgc gcc atg gcc gac caa gca cga acc atc        1008
Ile Arg Gln Ala Ile Thr Arg Ala Met Ala Asp Gln Ala Arg Thr Ile
                325                 330                 335 cgt atc cca gtc cac atg gtt gaa gtg atc aac aaa ctt ggt cgc atc        1056
Arg Ile Pro Val His Met Val Glu Val Ile Asn Lys Leu Gly Arg Ile
            340                 345                 350 caa cgt gaa ctc ctt cag gaa ctc ggc cgc gaa cca acc cca cag gaa        1104
Gln Arg Glu Leu Leu Gln Glu Leu Gly Arg Glu Pro Thr Pro Gln Glu
            355                 360                 365 ctg tcc aaa gaa atg gac atc tcc gag gaa aag gta ctg gaa atc cag        1152
Leu Ser Lys Glu Met Asp Ile Ser Glu Glu Lys Val Leu Glu Ile Gln
            370                 375                 380 cag tac gcc cgc gaa cca atc tcc ctg gac caa acc atc ggc gac gaa        1200
Gln Tyr Ala Arg Glu Pro Ile Ser Leu Asp Gln Thr Ile Gly Asp Glu
385                 390                 395                 400 ggc gac agc cag ctc ggc gac ttc atc gaa gac tcc gaa gcc gtc gtc        1248
Gly Asp Ser Gln Leu Gly Asp Phe Ile Glu Asp Ser Glu Ala Val Val
                405                 410                 415 gca gtc gac gcc gtc tca ttc acc ctg ctg caa gac cag cta cag gac        1296
Ala Val Asp Ala Val Ser Phe Thr Leu Leu Gln Asp Gln Leu Gln Asp
            420                 425                 430 gtc cta gag acc ctc tcc gaa cgt gaa gcc ggc gtg gtt aaa ctc cgc        1344
Val Leu Glu Thr Leu Ser Glu Arg Glu Ala Gly Val Val Lys Leu Arg
            435                 440                 445 ttc gga ctc acc gac gga atg cca cgc act tta gac gaa atc ggc caa        1392
Phe Gly Leu Thr Asp Gly Met Pro Arg Thr Leu Asp Glu Ile Gly Gln
450                 455                 460 gtt tac ggt gtc acc cgt gag cgc atc cgc cag att gag tcc aag acc        1440
Val Tyr Gly Val Thr Arg Glu Arg Ile Arg Gln Ile Glu Ser Lys Thr
465                 470                 475                 480 atg tct aag ctg cgc cac cca tca cgc tcc cag gtc ctt cgc gac tac        1488
Met Ser Lys Leu Arg His Pro Ser Arg Ser Gln Val Leu Arg Asp Tyr
                485                 490                 495 ctg gac taa                                                            1497
Leu Asp <210> SEQ ID NO 2
<211> LENGTH: 498
<212> TYPE: PRT
<213> ORGANISM: Corynebacterium glutamicum

<400> SEQUENCE: 2

Met Glu Ser Ser Met Val Glu Asn Asn Val Ala Lys Lys Thr Val Ala
1               5                   10                  15

Lys Lys Thr Ala Arg Lys Thr Ala Arg Lys Ala Ala Pro Arg Val Ala
            20                  25                  30

Thr Pro Leu Gly Val Ala Ser Glu Ser Pro Ile Ser Ala Thr Pro Ala
```

-continued

```
            35                  40                  45
Arg Ser Ile Asp Gly Thr Ser Thr Pro Val Glu Ala Ala Asp Thr Ile
 50                  55                  60

Glu Thr Thr Ala Pro Ala Ala Lys Ala Pro Ala Ala Lys Ala Pro Ala
 65                  70                  75                  80

Lys Lys Val Ala Lys Lys Thr Ala Arg Lys Ala Pro Ala Lys Lys Thr
                 85                  90                  95

Val Ala Lys Lys Ala Thr Thr Ala Lys Ala Ala Pro Ala Thr Ala Lys
                100                 105                 110

Asp Glu Asn Ala Pro Val Asp Asp Glu Glu Asn Leu Ala Gln Asp
                115                 120                 125

Glu Gln Asp Phe Asp Gly Asp Phe Val Asp Gly Ile Glu Asp Glu
                130                 135                 140

Glu Asp Glu Asp Gly Val Glu Ala Leu Gly Glu Ser Glu Asp Asp
 145                 150                 155                 160

Glu Glu Asp Gly Ser Ser Val Trp Asp Glu Asp Glu Ser Ala Thr Leu
                 165                 170                 175

Arg Gln Ala Arg Lys Asp Ala Glu Leu Thr Ala Ser Ala Asp Ser Val
                 180                 185                 190

Arg Ala Tyr Leu Lys Gln Ile Gly Lys Val Ala Leu Leu Asn Ala Glu
                 195                 200                 205

Gln Glu Val Ser Leu Ala Lys Arg Ile Glu Ala Gly Leu Tyr Ala Thr
                 210                 215                 220

His Arg Met Glu Glu Met Glu Glu Ala Phe Ala Ala Gly Asp Lys Asp
 225                 230                 235                 240

Ala Lys Leu Thr Pro Ala Val Lys Arg Asp Leu Arg Ala Ile Ala Arg
                 245                 250                 255

Asp Gly Arg Lys Ala Lys Asn His Leu Leu Glu Ala Asn Leu Arg Leu
                 260                 265                 270

Val Val Ser Leu Ala Lys Arg Tyr Thr Gly Arg Gly Met Ala Phe Leu
                 275                 280                 285

Asp Leu Ile Gln Glu Gly Asn Leu Gly Leu Ile Arg Ala Val Glu Lys
                 290                 295                 300

Phe Asp Tyr Ser Lys Gly Tyr Lys Phe Ser Thr Tyr Ala Thr Trp Trp
 305                 310                 315                 320

Ile Arg Gln Ala Ile Thr Arg Ala Met Ala Asp Gln Ala Arg Thr Ile
                 325                 330                 335

Arg Ile Pro Val His Met Val Glu Val Ile Asn Lys Leu Gly Arg Ile
                 340                 345                 350

Gln Arg Glu Leu Leu Gln Glu Leu Gly Arg Glu Pro Thr Pro Gln Glu
                 355                 360                 365

Leu Ser Lys Glu Met Asp Ile Ser Glu Glu Lys Val Leu Glu Ile Gln
 370                 375                 380

Gln Tyr Ala Arg Glu Pro Ile Ser Leu Asp Gln Thr Ile Gly Asp Glu
 385                 390                 395                 400

Gly Asp Ser Gln Leu Gly Asp Phe Ile Glu Asp Ser Glu Ala Val Val
                 405                 410                 415

Ala Val Asp Ala Val Ser Phe Thr Leu Leu Gln Asp Gln Leu Gln Asp
                 420                 425                 430

Val Leu Glu Thr Leu Ser Glu Arg Glu Ala Gly Val Val Lys Leu Arg
                 435                 440                 445

Phe Gly Leu Thr Asp Gly Met Pro Arg Thr Leu Asp Glu Ile Gly Gln
 450                 455                 460
```

US 7,524,657 B2

-continued

```
Val Tyr Gly Val Thr Arg Glu Arg Ile Arg Gln Ile Glu Ser Lys Thr
465                 470                 475                 480

Met Ser Lys Leu Arg His Pro Ser Arg Ser Gln Val Leu Arg Asp Tyr
                485                 490                 495

Leu Asp

<210> SEQ ID NO 3
<211> LENGTH: 1497
<212> TYPE: DNA
<213> ORGANISM: Corynebacterium glutamicum
<220> FEATURE:
<221> NAME/KEY: CDS
<222> LOCATION: (1)..(1494)
<223> OTHER INFORMATION: sigA allele
<220> FEATURE:
<221> NAME/KEY: mutation
<222> LOCATION: (1241)..(1241)
<223> OTHER INFORMATION: Exchange of cytosine for thymine

<400> SEQUENCE: 3 gtg gag agc agc atg gta gaa aac aac gta gca aaa aag acg gtc gct        48
Met Glu Ser Ser Met Val Glu Asn Asn Val Ala Lys Lys Thr Val Ala
1               5                   10                  15 aaa aag acc gca cgc aag acc gca cgc aaa gca gcc ccg cgc gtg gca        96
Lys Lys Thr Ala Arg Lys Thr Ala Arg Lys Ala Ala Pro Arg Val Ala
                20                  25                  30 acc cca ttg gga gtc gca tct gag tct ccc att tcg gcc acc cct gcg       144
Thr Pro Leu Gly Val Ala Ser Glu Ser Pro Ile Ser Ala Thr Pro Ala
            35                  40                  45 cgc agc atc gat gga acc tca acc cct gtt gaa gct gct gac acc ata       192
Arg Ser Ile Asp Gly Thr Ser Thr Pro Val Glu Ala Ala Asp Thr Ile
        50                  55                  60 gag acc acc gcc cct gca gcg aag gct cct gcg gcc aag gct ccc gct       240
Glu Thr Thr Ala Pro Ala Ala Lys Ala Pro Ala Ala Lys Ala Pro Ala
65                  70                  75                  80 aaa aag gtt gcc aag aag aca gct cgc aag gca cct gcg aaa aag act       288
Lys Lys Val Ala Lys Lys Thr Ala Arg Lys Ala Pro Ala Lys Lys Thr
                85                  90                  95 gtc gcc aag aaa gcc aca acc gcc aag gct gca cct gca act gcc aag       336
Val Ala Lys Lys Ala Thr Thr Ala Lys Ala Ala Pro Ala Thr Ala Lys
                100                 105                 110 gac gaa aac gca cct gtt gat gac gac gag gag aac ctc gct cag gat       384
Asp Glu Asn Ala Pro Val Asp Asp Asp Glu Glu Asn Leu Ala Gln Asp
            115                 120                 125 gaa cag gac ttc gac ggc gat gac ttc gta gac ggc atc gaa gac gaa       432
Glu Gln Asp Phe Asp Gly Asp Asp Phe Val Asp Gly Ile Glu Asp Glu
        130                 135                 140 gaa gat gaa gac ggc gtc gaa gcc ctc ggt gaa gaa agc gaa gac gac       480
Glu Asp Glu Asp Gly Val Glu Ala Leu Gly Glu Glu Ser Glu Asp Asp
145                 150                 155                 160 gaa gag gac ggc tca tcc gtt tgg gat gaa gac gaa tcc gca acc ctg       528
Glu Glu Asp Gly Ser Ser Val Trp Asp Glu Asp Glu Ser Ala Thr Leu
                165                 170                 175 cgt cag gca cgt aaa gat gcc gag ctc acc gct tcc gcc gac tct gtt       576
Arg Gln Ala Arg Lys Asp Ala Glu Leu Thr Ala Ser Ala Asp Ser Val
                180                 185                 190 cgc gct tac ctg aag caa atc ggt aaa gtt gcc ctg ctg aac gct gaa       624
Arg Ala Tyr Leu Lys Gln Ile Gly Lys Val Ala Leu Leu Asn Ala Glu
            195                 200                 205 cag gaa gtc tcc ctg gca aag cgc atc gaa gca ggc ctt tac gcc acc       672
Gln Glu Val Ser Leu Ala Lys Arg Ile Glu Ala Gly Leu Tyr Ala Thr
```

-continued

```
              210                 215                 220
cac cgc atg gag gaa atg gaa gaa gct ttc gca gcc ggt gac aag gac       720
His Arg Met Glu Glu Met Glu Glu Ala Phe Ala Ala Gly Asp Lys Asp
225                 230                 235                 240 gcg aaa ctc acc cca gcc gtc aag cgt gac ctc cgc gcc atc gct cgt       768
Ala Lys Leu Thr Pro Ala Val Lys Arg Asp Leu Arg Ala Ile Ala Arg
                245                 250                 255 gac ggc cgc aag gcg aaa aac cac ctc ctg gaa gcc aac ctt cgt ctg       816
Asp Gly Arg Lys Ala Lys Asn His Leu Leu Glu Ala Asn Leu Arg Leu
            260                 265                 270 gtt gtc tcc ctg gca aag cgc tac acc ggc cgt ggc atg gca ttc ctg       864
Val Val Ser Leu Ala Lys Arg Tyr Thr Gly Arg Gly Met Ala Phe Leu
        275                 280                 285 gac ctc atc cag gaa ggc aac ctc ggt ctg att cgt gcc gta gag aag       912
Asp Leu Ile Gln Glu Gly Asn Leu Gly Leu Ile Arg Ala Val Glu Lys
    290                 295                 300 ttc gac tac tcc aag ggc tac aag ttc tcc acc tac gca acc tgg tgg       960
Phe Asp Tyr Ser Lys Gly Tyr Lys Phe Ser Thr Tyr Ala Thr Trp Trp
305                 310                 315                 320 atc cgt cag gca atc acc cgc gcc atg gcc gac caa gca cga acc atc      1008
Ile Arg Gln Ala Ile Thr Arg Ala Met Ala Asp Gln Ala Arg Thr Ile
                325                 330                 335 cgt atc cca gtc cac atg gtt gaa gtg atc aac aaa ctt ggt cgc atc      1056
Arg Ile Pro Val His Met Val Glu Val Ile Asn Lys Leu Gly Arg Ile
            340                 345                 350 caa cgt gaa ctc ctt cag gaa ctc ggc cgc gaa cca acc cca cag gaa      1104
Gln Arg Glu Leu Leu Gln Glu Leu Gly Arg Glu Pro Thr Pro Gln Glu
        355                 360                 365 ctg tcc aaa gaa atg gac atc tcc gag gaa aag gta ctg gaa atc cag      1152
Leu Ser Lys Glu Met Asp Ile Ser Glu Glu Lys Val Leu Glu Ile Gln
    370                 375                 380 cag tac gcc cgc gaa cca atc tcc ctg gac caa acc atc ggc gac gaa      1200
Gln Tyr Ala Arg Glu Pro Ile Ser Leu Asp Gln Thr Ile Gly Asp Glu
385                 390                 395                 400 ggc gac agc cag ctc ggc gac ttc atc gaa gac tcc gaa gtc gtc gtc      1248
Gly Asp Ser Gln Leu Gly Asp Phe Ile Glu Asp Ser Glu Val Val Val
                405                 410                 415 gca gtc gac gcc gtc tca ttc acc ctg ctg caa gac cag cta cag gac      1296
Ala Val Asp Ala Val Ser Phe Thr Leu Leu Gln Asp Gln Leu Gln Asp
            420                 425                 430 gtc cta gag acc ctc tcc gaa cgt gaa gcc ggc gtg gtt aaa ctc cgc      1344
Val Leu Glu Thr Leu Ser Glu Arg Glu Ala Gly Val Val Lys Leu Arg
        435                 440                 445 ttc gga ctc acc gac gga atg cca cgc act tta gac gaa atc ggc caa      1392
Phe Gly Leu Thr Asp Gly Met Pro Arg Thr Leu Asp Glu Ile Gly Gln
    450                 455                 460 gtt tac ggt gtc acc cgt gag cgc atc cgc cag att gag tcc aag acc      1440
Val Tyr Gly Val Thr Arg Glu Arg Ile Arg Gln Ile Glu Ser Lys Thr
465                 470                 475                 480 atg tct aag ctg cgc cac cca tca cgc tcc cag gtc ctt cgc gac tac      1488
Met Ser Lys Leu Arg His Pro Ser Arg Ser Gln Val Leu Arg Asp Tyr
                485                 490                 495 ctg gac taa                                                           1497
Leu Asp
```

<210> SEQ ID NO 4
<211> LENGTH: 498
<212> TYPE: PRT
<213> ORGANISM: Corynebacterium glutamicum

<400> SEQUENCE: 4

```
Met Glu Ser Ser Met Val Glu Asn Val Ala Lys Lys Thr Val Ala
1               5                   10                  15

Lys Lys Thr Ala Arg Lys Thr Ala Arg Lys Ala Ala Pro Arg Val Ala
                20                  25                  30

Thr Pro Leu Gly Val Ala Ser Glu Ser Pro Ile Ser Ala Thr Pro Ala
            35                  40                  45

Arg Ser Ile Asp Gly Thr Ser Thr Pro Val Glu Ala Ala Asp Thr Ile
        50                  55                  60

Glu Thr Thr Ala Pro Ala Ala Lys Ala Pro Ala Ala Lys Ala Pro Ala
65                  70                  75                  80

Lys Lys Val Ala Lys Lys Thr Ala Arg Lys Ala Pro Ala Lys Lys Thr
                85                  90                  95

Val Ala Lys Lys Ala Thr Thr Ala Lys Ala Ala Pro Ala Thr Ala Lys
                100                 105                 110

Asp Glu Asn Ala Pro Val Asp Asp Glu Glu Asn Leu Ala Gln Asp
                115                 120                 125

Glu Gln Asp Phe Asp Gly Asp Asp Phe Val Asp Gly Ile Glu Asp Glu
        130                 135                 140

Glu Asp Glu Asp Gly Val Ala Leu Gly Glu Glu Ser Glu Asp Asp
145                 150                 155                 160

Glu Glu Asp Gly Ser Ser Val Trp Asp Glu Asp Ser Ala Thr Leu
                165                 170                 175

Arg Gln Ala Arg Lys Asp Ala Glu Leu Thr Ala Ser Ala Asp Ser Val
            180                 185                 190

Arg Ala Tyr Leu Lys Gln Ile Gly Lys Val Ala Leu Leu Asn Ala Glu
            195                 200                 205

Gln Glu Val Ser Leu Ala Lys Arg Ile Glu Ala Gly Leu Tyr Ala Thr
        210                 215                 220

His Arg Met Glu Glu Met Glu Glu Ala Phe Ala Ala Gly Asp Lys Asp
225                 230                 235                 240

Ala Lys Leu Thr Pro Ala Val Lys Arg Asp Leu Arg Ala Ile Ala Arg
                245                 250                 255

Asp Gly Arg Lys Ala Lys Asn His Leu Leu Glu Ala Asn Leu Arg Leu
            260                 265                 270

Val Val Ser Leu Ala Lys Arg Tyr Thr Gly Arg Gly Met Ala Phe Leu
        275                 280                 285

Asp Leu Ile Gln Glu Gly Asn Leu Gly Leu Ile Arg Ala Val Glu Lys
    290                 295                 300

Phe Asp Tyr Ser Lys Gly Tyr Lys Phe Ser Thr Tyr Ala Thr Trp Trp
305                 310                 315                 320

Ile Arg Gln Ala Ile Thr Arg Ala Met Ala Asp Gln Ala Arg Thr Ile
                325                 330                 335

Arg Ile Pro Val His Met Val Glu Val Ile Asn Lys Leu Gly Arg Ile
            340                 345                 350

Gln Arg Glu Leu Leu Gln Glu Leu Gly Arg Glu Pro Thr Pro Gln Glu
        355                 360                 365

Leu Ser Lys Glu Met Asp Ile Ser Glu Glu Lys Val Leu Glu Ile Gln
    370                 375                 380

Gln Tyr Ala Arg Glu Pro Ile Ser Leu Asp Gln Thr Ile Gly Asp Glu
385                 390                 395                 400

Gly Asp Ser Gln Leu Gly Asp Phe Ile Glu Asp Ser Glu Val Val Val
                405                 410                 415
```

```
Ala Val Asp Ala Val Ser Phe Thr Leu Leu Gln Asp Gln Leu Gln Asp
            420                 425                 430

Val Leu Glu Thr Leu Ser Glu Arg Glu Ala Gly Val Val Lys Leu Arg
        435                 440                 445

Phe Gly Leu Thr Asp Gly Met Pro Arg Thr Leu Asp Glu Ile Gly Gln
    450                 455                 460

Val Tyr Gly Val Thr Arg Glu Arg Ile Arg Gln Ile Glu Ser Lys Thr
465                 470                 475                 480

Met Ser Lys Leu Arg His Pro Ser Arg Ser Gln Val Leu Arg Asp Tyr
                485                 490                 495

Leu Asp

<210> SEQ ID NO 5
<211> LENGTH: 1892
<212> TYPE: DNA
<213> ORGANISM: Corynebacterium glutamicum
<220> FEATURE:
<221> NAME/KEY: CDS
<222> LOCATION: (226)..(1719)
<223> OTHER INFORMATION: sigA allele
<220> FEATURE:
<221> NAME/KEY: mutation
<222> LOCATION: (1466)..(1466)
<223> OTHER INFORMATION: Exchange of cytosine for thymine

<400> SEQUENCE: 5
tgatcggctg accaactcta taagagatgc acctcaagtt tggggatact tattcggcgt        60
ttctggggaa caaatacgtt tccctattgt tgtatatagg tattcgcact taagaaacat       120
ctctcatgga agaagctag gcggaaaggg cgttaagtac ttgccattta atcctcagca        180
tcactcggat cagtcggaga gtgtcgatgaa aatgcaccag gagcc gtg gag agc agc     237
                                                Val Glu Ser Ser
                                                 1 atg gta gaa aac aac gta gca aaa aag acg gtc gct aaa aag acc gca         285
Met Val Glu Asn Asn Val Ala Lys Lys Thr Val Ala Lys Lys Thr Ala
5                   10                  15                  20 cgc aag acc gca cgc aaa gca gcc ccg cgc gtg gca acc cca ttg gga         333
Arg Lys Thr Ala Arg Lys Ala Ala Pro Arg Val Ala Thr Pro Leu Gly
                25                  30                  35 gtc gca tct gag tct ccc att tcg gcc acc cct gcg cgc agc atc gat         381
Val Ala Ser Glu Ser Pro Ile Ser Ala Thr Pro Ala Arg Ser Ile Asp
        40                  45                  50 gga acc tca acc cct gtt gaa gct gct gac acc ata gag acc acc gcc         429
Gly Thr Ser Thr Pro Val Glu Ala Ala Asp Thr Ile Glu Thr Thr Ala
    55                  60                  65 cct gca gcg aag gct cct gcg gcc aag gct ccc gct aaa aag gtt gcc         477
Pro Ala Ala Lys Ala Pro Ala Ala Lys Ala Pro Ala Lys Lys Val Ala
70                  75                  80 aag aag aca gct cgc aag gca cct gcg aaa aag act gtc gcc aag aaa         525
Lys Lys Thr Ala Arg Lys Ala Pro Ala Lys Lys Thr Val Ala Lys Lys
85                  90                  95                  100 gcc aca acc gcc aag gct gca cct gca act gcc aag gac gaa aac gca         573
Ala Thr Thr Ala Lys Ala Ala Pro Ala Thr Ala Lys Asp Glu Asn Ala
            105                 110                 115 cct gtt gat gac gac gag gag aac ctc gct cag gat gaa cag gac ttc         621
Pro Val Asp Asp Asp Glu Glu Asn Leu Ala Gln Asp Glu Gln Asp Phe
        120                 125                 130 gac ggc gat gac ttc gta gac ggc atc gaa gac gaa gaa gat gaa gac         669
Asp Gly Asp Asp Phe Val Asp Gly Ile Glu Asp Glu Glu Asp Glu Asp
    135                 140                 145
```

```
ggc gtc gaa gcc ctc ggt gaa gaa agc gaa gac gac gaa gag gac ggc      717
Gly Val Glu Ala Leu Gly Glu Glu Ser Glu Asp Asp Glu Glu Asp Gly
    150                 155                 160 tca tcc gtt tgg gat gaa gac gaa tcc gca acc ctg cgt cag gca cgt      765
Ser Ser Val Trp Asp Glu Asp Glu Ser Ala Thr Leu Arg Gln Ala Arg
165                 170                 175                 180 aaa gat gcc gag ctc acc gct tcc gcc gac tct gtt cgc gct tac ctg      813
Lys Asp Ala Glu Leu Thr Ala Ser Ala Asp Ser Val Arg Ala Tyr Leu
                185                 190                 195 aag caa atc ggt aaa gtt gcc ctg ctg aac gct gaa cag gaa gtc tcc      861
Lys Gln Ile Gly Lys Val Ala Leu Leu Asn Ala Glu Gln Glu Val Ser
            200                 205                 210 ctg gca aag cgc atc gaa gca ggc ctt tac gcc acc cac cgc atg gag      909
Leu Ala Lys Arg Ile Glu Ala Gly Leu Tyr Ala Thr His Arg Met Glu
        215                 220                 225 gaa atg gaa gaa gct ttc gca gcc ggt gac aag gac gcg aaa ctc acc      957
Glu Met Glu Glu Ala Phe Ala Ala Gly Asp Lys Asp Ala Lys Leu Thr
    230                 235                 240 cca gcc gtc aag cgt gac ctc cgc gcc atc gct cgt gac ggc cgc aag     1005
Pro Ala Val Lys Arg Asp Leu Arg Ala Ile Ala Arg Asp Gly Arg Lys
245                 250                 255                 260 gcg aaa aac cac ctc ctg gaa gcc aac ctt cgt ctg gtt gtc tcc ctg     1053
Ala Lys Asn His Leu Leu Glu Ala Asn Leu Arg Leu Val Val Ser Leu
                265                 270                 275 gca aag cgc tac acc ggc cgt ggc atg gca ttc ctg gac ctc atc cag     1101
Ala Lys Arg Tyr Thr Gly Arg Gly Met Ala Phe Leu Asp Leu Ile Gln
            280                 285                 290 gaa ggc aac ctc ggt ctg att cgt gcc gta gag aag ttc gac tac tcc     1149
Glu Gly Asn Leu Gly Leu Ile Arg Ala Val Glu Lys Phe Asp Tyr Ser
        295                 300                 305 aag ggc tac aag ttc tcc acc tac gca acc tgg tgg atc cgt cag gca     1197
Lys Gly Tyr Lys Phe Ser Thr Tyr Ala Thr Trp Trp Ile Arg Gln Ala
    310                 315                 320 atc acc cgc gcc atg gcc gac caa gca cga acc atc cgt atc cca gtc     1245
Ile Thr Arg Ala Met Ala Asp Gln Ala Arg Thr Ile Arg Ile Pro Val
325                 330                 335                 340 cac atg gtt gaa gtg atc aac aaa ctt ggt cgc atc caa cgt gaa ctc     1293
His Met Val Glu Val Ile Asn Lys Leu Gly Arg Ile Gln Arg Glu Leu
                345                 350                 355 ctt cag gaa ctc ggc cgc gaa cca acc cca cag gaa ctg tcc aaa gaa     1341
Leu Gln Glu Leu Gly Arg Glu Pro Thr Pro Gln Glu Leu Ser Lys Glu
            360                 365                 370 atg gac atc tcc gag gaa aag gta ctg gaa atc cag cag tac gcc cgc     1389
Met Asp Ile Ser Glu Glu Lys Val Leu Glu Ile Gln Gln Tyr Ala Arg
        375                 380                 385 gaa cca atc tcc ctg gac caa acc atc ggc gac gaa ggc gac agc cag     1437
Glu Pro Ile Ser Leu Asp Gln Thr Ile Gly Asp Glu Gly Asp Ser Gln
    390                 395                 400 ctc ggc gac ttc atc gaa gac tcc gaa gtc gtc gtc gca gtc gac gcc     1485
Leu Gly Asp Phe Ile Glu Asp Ser Glu Val Val Val Ala Val Asp Ala
405                 410                 415                 420 gtc tca ttc acc ctg ctg caa gac cag cta cag gac gtc cta gag acc     1533
Val Ser Phe Thr Leu Leu Gln Asp Gln Leu Gln Asp Val Leu Glu Thr
                425                 430                 435 ctc tcc gaa cgt gaa gcc ggc gtg gtt aaa ctc cgc ttc gga ctc acc     1581
Leu Ser Glu Arg Glu Ala Gly Val Val Lys Leu Arg Phe Gly Leu Thr
            440                 445                 450 gac gga atg cca cgc act tta gac gaa atc ggc caa gtt tac ggt gtc     1629
Asp Gly Met Pro Arg Thr Leu Asp Glu Ile Gly Gln Val Tyr Gly Val
```

```
                              455                 460                 465
acc cgt gag cgc atc cgc cag att gag tcc aag acc atg tct aag ctg     1677
Thr Arg Glu Arg Ile Arg Gln Ile Glu Ser Lys Thr Met Ser Lys Leu
    470                 475                 480 cgc cac cca tca cgc tcc cag gtc ctt cgc gac tac ctg gac             1719
Arg His Pro Ser Arg Ser Gln Val Leu Arg Asp Tyr Leu Asp
485                 490                 495 taaaacccca gtcgggctca agaccgggcc gccactgttt cctctgcgg ggaacggtgg    1779 tggcccggtt tttctgttgc tttggttcgg ctggtcacag ttcggctggg gtgttttaag   1839
tttgatttca cattgccgat ttctaaacgc cgagttctcg gattcgagac ctt          1892

<210> SEQ ID NO 6
<211> LENGTH: 498
<212> TYPE: PRT
<213> ORGANISM: Corynebacterium glutamicum

<400> SEQUENCE: 6

Val Glu Ser Ser Met Val Glu Asn Asn Val Ala Lys Lys Thr Val Ala
1               5                   10                  15

Lys Lys Thr Ala Arg Lys Thr Ala Arg Lys Ala Ala Pro Arg Val Ala
            20                  25                  30

Thr Pro Leu Gly Val Ala Ser Glu Ser Pro Ile Ser Ala Thr Pro Ala
        35                  40                  45

Arg Ser Ile Asp Gly Thr Ser Thr Pro Val Glu Ala Ala Asp Thr Ile
    50                  55                  60

Glu Thr Thr Ala Pro Ala Ala Lys Ala Pro Ala Ala Lys Ala Pro Ala
65                  70                  75                  80

Lys Lys Val Ala Lys Lys Thr Ala Arg Lys Ala Pro Ala Lys Lys Thr
                85                  90                  95

Val Ala Lys Lys Ala Thr Thr Ala Lys Ala Ala Pro Ala Thr Ala Lys
            100                 105                 110

Asp Glu Asn Ala Pro Val Asp Asp Glu Glu Asn Leu Ala Gln Asp
        115                 120                 125

Glu Gln Asp Phe Asp Gly Asp Phe Val Asp Gly Ile Glu Asp Glu
    130                 135                 140

Glu Asp Glu Asp Gly Val Glu Ala Leu Gly Glu Ser Glu Asp Asp
145                 150                 155                 160

Glu Glu Asp Gly Ser Ser Val Trp Asp Glu Asp Glu Ser Ala Thr Leu
                165                 170                 175

Arg Gln Ala Arg Lys Asp Ala Glu Leu Thr Ala Ser Ala Asp Ser Val
            180                 185                 190

Arg Ala Tyr Leu Lys Gln Ile Gly Lys Val Ala Leu Leu Asn Ala Glu
        195                 200                 205

Gln Glu Val Ser Leu Ala Lys Arg Ile Glu Ala Gly Leu Tyr Ala Thr
    210                 215                 220

His Arg Met Glu Glu Met Glu Glu Ala Phe Ala Ala Gly Asp Lys Asp
225                 230                 235                 240

Ala Lys Leu Thr Pro Ala Val Lys Arg Asp Leu Arg Ala Ile Ala Arg
                245                 250                 255

Asp Gly Arg Lys Ala Lys Asn His Leu Leu Glu Ala Asn Leu Arg Leu
            260                 265                 270

Val Val Ser Leu Ala Lys Arg Tyr Thr Gly Arg Gly Met Ala Phe Leu
        275                 280                 285

Asp Leu Ile Gln Glu Gly Asn Leu Gly Leu Ile Arg Ala Val Glu Lys
```

-continued

```
              290             295             300
Phe Asp Tyr Ser Lys Gly Tyr Lys Phe Ser Thr Tyr Ala Thr Trp Trp
305                 310                 315                 320

Ile Arg Gln Ala Ile Thr Arg Ala Met Ala Asp Gln Ala Arg Thr Ile
                325                 330                 335

Arg Ile Pro Val His Met Val Glu Val Ile Asn Lys Leu Gly Arg Ile
            340                 345                 350

Gln Arg Glu Leu Leu Gln Glu Leu Gly Arg Glu Pro Thr Pro Gln Glu
        355                 360                 365

Leu Ser Lys Glu Met Asp Ile Ser Glu Glu Lys Val Leu Glu Ile Gln
370                 375                 380

Gln Tyr Ala Arg Glu Pro Ile Ser Leu Asp Gln Thr Ile Gly Asp Glu
385                 390                 395                 400

Gly Asp Ser Gln Leu Gly Asp Phe Ile Glu Asp Ser Glu Val Val Val
                405                 410                 415

Ala Val Asp Ala Val Ser Phe Thr Leu Leu Gln Asp Gln Leu Gln Asp
                420                 425                 430

Val Leu Glu Thr Leu Ser Glu Arg Glu Ala Gly Val Val Lys Leu Arg
            435                 440                 445

Phe Gly Leu Thr Asp Gly Met Pro Arg Thr Leu Asp Glu Ile Gly Gln
        450                 455                 460

Val Tyr Gly Val Thr Arg Glu Arg Ile Arg Gln Ile Glu Ser Lys Thr
465                 470                 475                 480

Met Ser Lys Leu Arg His Pro Ser Arg Ser Gln Val Leu Arg Asp Tyr
                485                 490                 495

Leu Asp
```

<210> SEQ ID NO 7
<211> LENGTH: 1689
<212> TYPE: DNA
<213> ORGANISM: Artificial sequence
<220> FEATURE:
<221> NAME/KEY: misc_feature
<222> LOCATION: (1)..(1689)
<223> OTHER INFORMATION: Description of the artificial sequence:
      PCR product containing an n 3'-terminal region of the sigA
      allele (= sigA_A414V allele) and the downstream region
<220> FEATURE:
<221> NAME/KEY: mutation
<222> LOCATION: (854)..(854)
<223> OTHER INFORMATION: Exchange of cytosine for thymine

<400> SEQUENCE: 7

```
acgaattccg acggcgatga cttcgtagac ggcatcgaag acgaagaaga tgaagacggc      60
gtcgaagccc tcggtgaaga aagcgaagac gacgaagagg acggctcatc cgtttgggat     120
gaagacgaat ccgcaaccct gcgtcaggca cgtaaagatg ccgagctcac cgcttccgcc     180
gactctgttc gcgcttacct gaagcaaatc ggtaaagttg ccctgctgaa cgctgaacag     240
gaagtctccc tggcaaagcg catcgaagca ggccttacg ccacccaccg catggaggaa     300
atggaagaag ctttcgcagc cggtgacaag gacgcgaaac tcaccccagc cgtcaagcgt     360
gacctccgcg ccatcgctcg tgacggccgc aaggcgaaaa accacctcct ggaagccaac     420
cttcgtctgg ttgtctccct ggcaaagcgc tacaccggcc gtggcatggc attcctggac     480
ctcatccagg aaggcaacct cggtctgatt cgtgccgtag agaagttcga ctactccaag     540
ggctacaagt tctccaccta cgcaacctgg tggatccgtc aggcaatcac ccgcgccatg     600
gccgaccaag cacgaaccat ccgtatccca gtccacatgg ttgaagtgat caacaaactt     660
```

```
ggtcgcatcc aacgtgaact ccttcaggaa ctcggccgcg aaccaacccc acaggaactg      720
tccaaagaaa tggacatctc cgaggaaaag gtactggaaa tccagcagta cgcccgcgaa      780
ccaatctccc tggaccaaac catcggcgac gaaggcgaca gccagctcgg cgacttcatc      840
gaagactccg aagtcgtcgt cgcagtcgac gccgtctcat tcaccctgct gcaagaccag      900
ctacaggacg tcctagagac cctctccgaa cgtgaagccg gcgtggttaa actccgcttc      960
ggactcaccg acggaatgcc acgcacttta gacgaaatcg gccaagttta cggtgtcacc     1020
cgtgagcgca tccgccagat tgagtccaag accatgtcta agctgcgcca cccatcacgc     1080
tcccaggtcc ttcgcgacta cctggactaa aaccccagtc gggctcaaga ccgggccgcc     1140
actgttttcc tctgcgggga acggtggtgg cccggttttt ctgttgcttt ggttcggctg     1200
gtcacagttc ggctggggtg ttttaagttt gatttcacat tgccgatttc taaacgccga     1260
gttctcggat tcgagacctt acctgcaatt tcacggttac aatttctcgt tagcactttc     1320
gcgtactcaa tttcttatgt tcaatttcgg tcggaaaagt gccattttcc gacatcgcct     1380
tgagaaattg aatacaagaa attgagcgca aggtatcgaa cttgagaaat tgagctttag     1440
cactcactcc cctgtttgat gaagtcagca aagccaaaag acgacttcac atctccgact     1500
tcttaacagc gacttctcgt ggctgacttc gctacctaaa cctgagtttc cttagcgaag     1560
tcgtgtgatg agaagtcgtg tgatgagaag ttgggtatga gaagtcagca cacgtgaagt     1620
cgccttttct ccccggcacg ctcggagtag cgtgaaaggt ggaatggagc gaggtggaac     1680
ggaattcca                                                             1689
```

<210> SEQ ID NO 8
<211> LENGTH: 20
<212> TYPE: DNA
<213> ORGANISM: Artificial sequence
<220> FEATURE:
<221> NAME/KEY: misc_feature
<222> LOCATION: (1)..(20)
<223> OTHER INFORMATION: Description of the artificial sequence:
      primer sigA-1

<400> SEQUENCE: 8
tgatcggctg accaactcta                                                   20

<210> SEQ ID NO 9
<211> LENGTH: 20
<212> TYPE: DNA
<213> ORGANISM: Artificial sequence
<220> FEATURE:
<221> NAME/KEY: misc_feature
<222> LOCATION: (1)..(20)
<223> OTHER INFORMATION: Description of the artificial sequence:
      primer sigA-2

<400> SEQUENCE: 9
aaggtctcga atccgagaac                                                   20

<210> SEQ ID NO 10
<211> LENGTH: 28
<212> TYPE: DNA
<213> ORGANISM: Artificial sequence
<220> FEATURE:
<221> NAME/KEY: misc_feature
<222> LOCATION: (1)..(28)
<223> OTHER INFORMATION: Description of the artificial sequence:
      primer sigA_XL-A1

<400> SEQUENCE: 10

-continued

```
acgaattccg acggcgatga cttcgtag                                          28

<210> SEQ ID NO 11
<211> LENGTH: 28
<212> TYPE: DNA
<213> ORGANISM: Artificial sequence
<220> FEATURE:
<221> NAME/KEY: misc_feature
<222> LOCATION: (1)..(28)
<223> OTHER INFORMATION: Description of the artificial sequence:
      primer sigA_XL-A2

<400> SEQUENCE: 11
tggaattccg ttccacctcg ctccattc                                          28

<210> SEQ ID NO 12
<211> LENGTH: 20
<212> TYPE: DNA
<213> ORGANISM: Artificial sequence
<220> FEATURE:
<221> NAME/KEY: misc_feature
<222> LOCATION: (1)..(20)
<223> OTHER INFORMATION: Description of the artificial sequence:
      primer sA_1

<400> SEQUENCE: 12
aagttctcca cctacgcaac                                                   20
```

US 7,524,657 B2

ALLELES OF THE SIGA GENE FROM CORYNEFORM BACTERIA

CROSS REFERENCE TO RELATED APPLICATIONS

The present application represents U.S. national stage of international application PCT/EP02/11561, which had an international filing date of Oct. 16, 2002 and which was published in English under PCT Article 21(2) on Jul. 3, 2003. The international application claims priority to German application 101 62 729.7, filed on Dec. 20, 2001.

FIELD OF THE INVENTION

The invention provides alleles of the sigA gene from coryneform bacteria which code for variants of sigma factor A and a process for the fermentative preparation of L-lysine using bacteria which contain these alleles.

PRIOR ART

The amino acid L-lysine is used in human medicine and in the pharmaceuticals industry, in the foodstuffs industry and very particularly in animal nutrition.

It is known that amino acids are prepared by fermentation from strains of coryneform bacteria, in particular *Corynebacterium glutamicum*. Because of their great importance, work is constantly being undertaken to improve the preparation processes. Improvements to the process can relate to fermentation measures, such as, for example, stirring and supply of oxygen, or the composition of the nutrient media, such as, for example, the sugar concentration during the fermentation, or the working up to the product form by, for example, ion exchange chromatography, or the intrinsic output properties of the microorganism itself.

Methods of mutagenesis, selection and mutant selection are used to improve the output properties of these microorganisms. Strains which are resistant to antimetabolites or are auxotrophic for metabolites of regulatory importance and which produce amino acids are obtained in this manner. A known antimetabolite is the lysine analogue S-(2-aminoethyl)-L-cysteine (AEC).

Methods of the recombinant DNA technique have also been employed for some years for improving the strain of *Corynebacterium* strains which produce L-amino acid, by amplifying individual amino acid biosynthesis genes and investigating the effect on the amino acid production.

The nucleotide sequence of the gene which codes for sigma factor A from *Corynebacterium glutamicum* can be found in the patent application EP-A-1108790 as sequence no. 2100 and as sequence no. 7065.

The nucleotide sequence is also deposited in the databank of the National Center for Biotechnology Information (NCBI) of the National Library of Medicine (Bethesda, Md., USA) under Accession Number AX122184 and under Accession Number AX127149.

OBJECT OF THE INVENTION

The inventors had the object of providing new measures for improved fermentative preparation of L-lysine.

SUMMARY OF THE INVENTION

When L-lysine or lysine are mentioned in the following, not only the bases but also the salts, such as e.g. lysine monohydrochloride or lysine sulfate, are meant by this.

The invention provides replicatable nucleotide sequences (DNA) which originate from coryneform bacteria, in particular *Corynebacterium glutamicum*, and code for sigma factor A, wherein the associated amino acid sequences in SEQ ID No. 2 contains any proteinogenic amino acid excluding L-alanine at position 414.

The invention furthermore provides a replicatable nucleotide sequence (DNA) which originates from coryneform bacteria, in particular *Corynebacterium glutamicum*, and codes for sigma factor A, wherein the associated amino acid sequence contains L-valine at position 414, shown in SEQ ID No. 4.

The invention furthermore provides a replicatable nucleotide sequence (DNA) which originates from coryneform bacteria, in particular *Corynebacterium glutamicum*, and codes for sigma factor A, the base sequence of which contains thymine at position 1241, shown in SEQ ID No. 3.

The invention furthermore provides plasmids (vectors) which contain the nucleotide sequences according to the invention and optionally replicate in coryneform bacteria.

The invention furthermore provides coryneform bacteria which contain the nucleotide sequences according to the invention and in which the nucleotide sequences which code for sigma factor A are optionally present in over-expressed form, wherein the associated amino acid sequences contain another proteinogenic amino acid at position 414 of SEQ ID No. 2.

Over-expression is understood as meaning an increase in the intracellular concentration or activity of the sigma actors A according to the invention.

By over-expression measures, the activity or concentration of the corresponding protein is in general increased by at least 10%, 25%, 50%, 75%, 100%, 150%, 200%, 300%, 400% or 500%, up to a maximum of 1000% or 2000%, based on the activity or concentration of the protein in the starting microorganism.

Sigma factor A is a transcription factor which mediates the binding of RNA polymerase to specific sites (initiation sites) of the DNA and initiates the start (initiation) of transcription. It participates in the initiation of transcription a large number of genes, for example the genes hom, which codes for homoserine dehydrogenase, gap, which codes for glyceraldehyde 3-phosphate dehydrogenase, fda, which codes for fructose bisphosphate aldolase, and pgk, which codes for phosphoglycerate kinase (Pátek et al., Microbiology 143: 1297-1309 (1996)).

To achieve an over-expression, the number of copies of the corresponding genes can be increased, or the promoter and regulation region or the ribosome binding site upstream of the structural gene can be mutated. Expression cassettes which are incorporated upstream of the structural gene act in the same way. By inducible promoters, it is additionally possible to increase the expression in the course of fermentative L-lysine production. The expression is likewise improved by measures to prolong the life of the m-RNA. Furthermore, the enzyme activity is also increased by preventing the degradation of the enzyme protein. The genes or gene constructs can either be present in plasmids with a varying number of copies, or can be integrated and amplified in the chromosome. Alternatively, an over-expression of the genes in question can furthermore be achieved by changing the composition of the media and the culture procedure.

Plasmids which are replicated in coryneform bacteria are suitable for increasing the number of copies of the sigA alleles according to the invention. Numerous known plasmid vectors, such as e.g. pZ1 (Menkel et al., Applied and Environmental Microbiology (1989) 64: 549-554), pEKEx1 (Eikmanns et al., Gene 102:93-98 (1991)) or pHS2-1 (Sonnen et al., Gene107:69-74 (1991)) are based on the cryptic plasmids pHM1519, pBL1 or pGA1. Other plasmid vectors, such as e.g. those based on pCG4 (U.S. Pat. No. 4,489,160), or pNG2 (Serwold-Davis et al., FEMS Microbiology Letters 66, 119-124 (1990)), or pAG1 (U.S. Pat. No. 5,158,891) can be used in the same manner.

The method of chromosomal gene amplification, such as has been described, for example, by Reinscheid et al. (Applied and Environmental Microbiology 60, 126-132 (1994)) for duplication or amplification of the hom-thrB operon, can furthermore be used to increase the number of copies. In this method, the complete gene or allele is cloned in a plasmid vector which can replicate in a host (typically *E. coli*), but not in *C. glutamicum*. Possible vectors are, for example, pSUP301 (Simon et al., Bio/Technology 1, 784-791 (1983)), pK18mob or pK19mob (Schäfer et al., Gene 145, 69-73 (1994)), pGEM-T (Promega Corporation, Madison, Wis., USA), pCR2.1-TOPO (Shuman, Journal of Biological Chemistry 269:32678-84 (1994); U.S. Pat. No. 5,487,993), pCR®Blunt (Invitrogen, Groningen, Holland; Bernard et al., Journal of Molecular Biology, 234: 534-541 (1993)), pEM1 (Schrumpf et al., Journal of Bacteriology 173:4510-4516 (1991)) or pBGS8 (Spratt et al., Gene 41: 337-342 (1986)). The plasmid vector which contains the gene or allele to be amplified is then transferred into the desired strain of *C. glutamicum* by conjugation or transformation. The method of conjugation is described, for example, by Schäfer et al. (Applied and Environmental Microbiology 60, 756-759 (1994)). Methods for transformation are described, for example, by Thierbach et al. (Applied Microbiology and Biotechnology 29, 356-362 (1988)), Dunican and Shivnan (Bio/Technology 7, 1067-1070 (1989)) and Tauch et al. (FEMS Microbiological Letters 123, 343-347 (1994)). After homologous recombination by means of a "cross over" event, the resulting strain contains at least two copies of the gene or allele in question.

The increase in protein concentration is detectable via 1- and 2-dimensional protein gel separation and subsequent optical identification of the protein concentration in the gel with appropriate evaluation software. A common method for preparation of the protein gels in the case of coryneform bacteria and for identification of the proteins is the procedure described by Hermann et al. (Electrophoresis, 22:1712-23 (2001)). The protein concentration can also be analysed by western blot hybridization with an antibody specific for the protein to be detected (Sambrook et al., Molecular cloning: a laboratory manual. 2$^{nd}$ Ed. Cold Spring Harbor Laboratory Press, Cold Spring Harbor, N.Y., 1989) and subsequent optical evaluation with appropriate software for determination of the concentration (Lohaus and Meyer (1998) Biospektrum 5:32-39; Lottspeich (1999) Angewandte Chemie 111:2630-2647). The activity of DNA-binding proteins can be measured by means of DNA band shift assays (also called gel retardation) (Wilson et al. (2001) Journal of Bacteriology 183:2151-2155). The effect of DNA-binding proteins on the expression of other genes can be detected by various well-described methods of reporter gene assay (Sambrook et al., Molecular cloning: a laboratory manual. 2$^{nd}$ Ed. Cold Spring Harbor Laboratory Press, Cold Spring Harbor, N.Y., 1989).

The invention provides replicatable, preferably endogenous nucleotide sequences (DNA) which originate from coryneform bacteria and code for the protein sigma factor. A, wherein in the associated amino acid sequences the L-alanine at position 414 of SEQ ID No. 2 is replaced by another proteinogenic amino acid, in particular L-valine, shown in SEQ ID No. 4.

The invention also provides replicatable, preferably endogenous nucleotide sequences (DNA) which originate from coryneform bacteria and code for the protein sigma factor A, the associated base sequence of which contains thymine at position 1241, shown in SEQ ID No. 3.

"Endogenous genes" or "endogenous nucleotide sequences" are understood as meaning the genes or nucleotide sequences present in the population of a species.

The invention also provides vectors (plasmids) which contain the nucleotide sequences mentioned and optionally replicate in coryneform bacteria.

Coryneform bacteria which preferably contain the nucleotide sequence(s) mentioned according to the nucleotide sequences which code for sigma factor A in an over-expressed form are also claimed.

The invention provides a process for the preparation of L-lysine or feedstuffs additives comprising L-lysine in which in general the following steps are carried out:
a) fermentation of coryneform bacteria which contain endogenous nucleotide sequences which code for sigma factor A, wherein in the associated amino acid sequences the L-alanine at position 414 is replaced by another proteinogenic amino acid, preferably L-valine,
the alleles of the endogenous sigA gene are over-expressed under conditions suitable for the formation of the sigA gene product sigma factor A,
b) concentration of the L-lysine in the fermentation broth,
c) isolation of the L-lysine or feedstuffs additive comprising L-lysine from the fermentation broth, optionally
d) with constituents from the fermentation broth and/or the biomass (>0 to 100%).

Proteinogenic amino acids are to be understood as meaning all amino acids which are constituents of proteins or polypeptides. These are, in particular: L-aspartic acid, L-asparagine, L-threonine, L-serine, L-glutamic acid, L-glutamine, glycine, L-alanine, L-cysteine, L-valine, L-methionine, L-isoleucine, L-leucine, L-tyrosine, L-phenylalanine, L-histidine, L-lysine, L-tryptophan, L-proline and L-arginine.

The wild-type form of the sigA genesis contained in wild-type strains of coryneform bacteria, in particular of the genus *corynebacterium*. It is shown in SEQ ID No. 1. The wild-type protein is shown in SEQ ID No. 2.

Of the genus *Corynebacterium*, the species *Corynebacterium glutamicum* known to experts is to be mentioned in particular. Known wild-type strains of the species *Corynebacterium glutamicum* are, for example

*Corynebacterium glutamicum* ATCC13032
*Corynebacterium acetoglutamicum* ATCC15806
*Corynebacterium acetoacidophilum* ATCC13870
*Corynebacterium melassecola* ATCC17965
*Corynebacterium thermoaminogenes* FERM BP-1539
*Brevibacterium flavum* ATCC14067
*Brevibacterium lactofermentum* ATCC13869 and
*Brevibacterium divaricatum* ATCC14020.

Strains with the designation "ATCC" can be obtained from the American Type Culture Collection (Manassas, Va., USA). Strains with the designation "FERM" can be obtained from the National Institute of Advanced Industrial Science and Technology (AIST Tsukuba Central 6, 1-1-1 Higashi, Tsukuba Ibaraki, Japan). The strain of *Corynebacterium thermoaminogenes* mentioned (FERM BP-1539) and others (FERM BP-1540, FERM BP-1541 and FERM BP-1542) are described in U.S. Pat. No. 5,250,434.

To produce the sigA alleles according to the invention which code for variants of sigma factor A characterized by an amino acid exchange at position 414 of SEQ ID No. 2, mutagenesis methods described in the prior art are used.

Conventional in vivo mutagenesis methods using mutagenic substances, such as, for example, N-methyl-N'-nitro-N-nitrosoguanidine, or ultraviolet light can be used for the mutagenesis.

In vitro methods, such as, for example, a treatment with hydroxylamine (Miller, J. H.: A Short Course in Bacterial Genetics. A Laboratory Manual and Handbook for *Escherichia coli* and Related Bacteria, Cold Spring Harbor Laboratory Press, Cold Spring Harbor, 1992) or mutagenic oligonucleotides. (T. A. Brown: Gentechnologie für Einsteiger [Genetic Engineering for Beginners], Spektrum Akademischer Verlag, Heidelberg, 1993) or the polymerase chain reaction (PCR) such as is described in the handbook by Newton and Graham (PCR, Spektrum Akademischer Verlag, Heidelberg, 1994) can furthermore be used for the mutagenesis.

Further instructions on generation of mutations can be found in the prior art and in known textbooks of genetics and molecular biology, such as e.g. the textbook by Knippers ("Molekulare Genetik", 6th edition, Georg Thieme Verlag, Stuttgart, Germany, 1995), that by Winnacker ("Gene und Klone", VCH Verlagsgesellschaft, Weinheim, Germany, 1990) or that by Hagemann ("Allgemeine Genetik", Gustav Fischer Verlag, Stuttgart, 1986).

If in vitro methods are used, the sigA gene described in the prior art is amplified starting from isolated complete DNA of a wild-type strain with the aid of the polymerase chain reaction, optionally cloned in suitable plasmid vectors, and the DNA is then subjected to the mutagenesis process. Instructions for amplification of DNA sequences with the aid of the polymerase chain reaction (PCR) can be found by the expert, inter alia, in the handbook by Gait: Oligonucleotide Synthesis: A Practical Approach (IRL Press, Oxford, UK, 1984) and in Newton and Graham: PCR (Spektrum Akademischer Verlag, Heidelberg, Germany, 1994). Suitable sigA alleles are then selected by the processes described above and investigated.

The invention provides a new sigA allele which codes for a variant of sigma factor A and is shown in SEQ ID No. 3. The sigA alleles according to the invention can be transferred into suitable strains by the method of gene replacement, such as is described by Schwarzer and Pühler (Bio/Technology 9, 84-87 (1991)) or Peters-Wendisch et al. (Microbiology 144, 915-927 (1998)). The corresponding sigA allele is cloned here in a vector which is not replicative for *C. glutamicum*, such as, for example, pK18mobsacB or pK19mobsacB (Jäger et al., Journal of Bacteriology 174: 5462-65 (1992)) or pCR®Blunt (Invitrogen, Groningen, Holland; Bernard et al., Journal of Molecular Biology, 234: 534-541 (1993)) and this is then transferred into the desired host of *C. glutamicum* by transformation or conjugation. After homologous recombination by means of a first "cross-over" event which effects integration and a suitable second "cross-over" event which effects excision in the target gene or in the target sequence, the incorporation of the mutation is achieved.

In addition, it may be advantageous for the production of L-amino acids at the same time to enhance, in particular over-express one or more enzymes of the particular biosynthesis pathway, of glycolysis, of anaplerosis, of the citric acid cycle, of the pentose phosphate cycle, of amino acid export and optionally regulatory proteins, in addition to the use of the sigA allele according to the invention. The use of endogenous genes is in general preferred.

"Endogenous genes" or "endogenous nucleotide sequences" are understood as meaning the genes or nucleotide sequences and alleles thereof present in the population of a species.

The term "enhancement" in this connection describes the increase in the intracellular activity or concentration of one or more enzymes or proteins in a microorganism which are coded by the corresponding DNA, for example by increasing the number of copies of the gene or genes, using a potent promoter or using a gene or allele which codes for a corresponding enzyme or protein having a high activity, and optionally combining these measures. An increase in the activity of the corresponding enzyme protein can also be effected by a reduced sensitivity to inhibitors.

By enhancement measures, in particular over-expression, the activity or concentration of the corresponding protein is in general increased by at least 10%, 25%, 50%, 75%, 100%, 150%, 200%, 300%, 400% or 500%, up to a maximum of 1000% or 2000%, based on that of the wild-type protein or the activity or concentration of the protein in the starting microorganism.

Thus, for the preparation of L-lysine, in addition to the use of the variants of the sigA gene, at the same time one or more of the endogenous genes chosen from the group consisting of
- the dapA gene which codes for dihydrodipicolinate synthase (EP-B 0 197 335),
- the gap gene which codes for glyceraldehyde 3-phosphate dehydrogenase (Eikmanns (1992), Journal of Bacteriology 174:6076-6086),
- the eno gene which codes for enolase (DE: 19947791.4),
- the tpi gene which codes for triose phosphate isomerase (Eikmanns (1992), Journal of Bacteriology 174:6076-6086),
- the pgk gene which codes for 3-phosphoglycerate kinase (Eikmanns (1992), Journal of Bacteriology 174:6076-6086),
- the zwf gene which codes for glucose 6-phosphate dehydrogenase (JP-A-09224661, EP-A-1108790),
- the pyc gene which codes for pyruvate carboxylase (DE-A-198 31 609; EP-A1108790),
- the mqo gene which codes for malate-quinone oxidoreductase (Molenaar et al., European Journal of Biochemistry 254, 395-403 (1998)),
- the lysC gene which codes for a feed-back resistant aspartate kinase (Accession No. P26512; EP-B-0387527; EP-A-0699759; WO 00/63388),
- the lysE gene which codes for the lysine export protein (DE-A-195 48 222),
- the zwa1 gene which codes for the Zwa1 protein (DE: 19959328,0, DSM 13115)
- the gnd gene which codes for 6-phosphogluconate dehydrogenase (WO 01/71012),
- the opcA gene which codes for a sub-unit of glucose 6-phosphate dehydrogenase (sequence no. 79 from WO 01/00844; WO 01/04322), can be enhanced, in particular over-expressed.

The enhancement of 6-phosphogluconate dehydrogenase can also be achieved, inter alia, by amino acid exchanges, such as, for example, by exchange of L-proline for L-serine, L-leucine, L-isoleucine or L-threonine at position 158 of the enzyme protein and/or by exchange of L-serine for L-phenylalanine or L-tyrosine at position 361 of the enzyme protein.

The enhancement of the glucose 6-phosphate dehydrogenase sub-unit can also be achieved, inter alia, by amino acid exchanges, such as, for example, by exchange of L-serine by L-phenylalanine or L-tyrosine at position 312 of the enzyme protein.

It may be furthermore advantageous for the production of L-lysine, in addition to the use of the variants of the sigA gene, at the same time for one or more of the endogenous genes chosen from the group consisting of

- the pck gene which codes for phosphoenol pyruvate carboxykinase (DE 199 50 409.1, DSM 13047),
- the pgi gene which codes for glucose 6-phosphate isomerase (U.S. Ser. No. 09/396,478, DSM 12969),
- the poxB gene which codes for pyruvate oxidase (DE:1995 1975.7, DSM 13114),
- the zwa2 gene which codes for the $Zwa^2$ protein (DE: 19959327,2, DSM 13113),
- the fda gene which codes for fructose 1,6-bisphosphate aldolase (Accession No. X17313; von der Osten et al., Molecular Microbiology 3 (11), 1625-1637 (1989)),
- the hom gene which codes for homoserine dehydrogenase (EP-A -0131171),
- the leuB gene which codes for isopropyl malate dehydrogenase (Pátek et al., Applied Environmental Microbiology 50:43-47(1989)), Accession No. Y09578),
- the leuC gene which codes for isopropyl malate dehydratase (Accession No. AX121536, sequence no. 1452 from patent EP1108790, Accession No. AX063983, sequence no. 265 from patent WO0100843),
- the thrB gene which codes for homoserine kinase (Peoples, O. W., et al., Molecular Microbiology 2:63-72(1988)) and
- the pfkB gene which codes for phosphofructokinase (SEQ ID No. 57 from WO 01/00844)

to be attenuated, in particular for the expression thereof to be reduced.

The term "attenuation" in this connection describes the reduction or elimination of the intracellular activity of one or more enzymes or proteins in a microorganism which are coded by the corresponding DNA, for example by using a weak promoter or using a gene or allele which codes for a corresponding enzyme with a low activity or inactivates the corresponding gene or enzyme or protein, and optionally combining these measures.

By attenuation measures, the activity or concentration of the corresponding protein is in general reduced to 0 to 75%, 0 to 50%, 0 to 25%, 0 to 10% or 0 to 5% of the activity or concentration of the wild-type protein or of the activity or concentration of the protein in the starting microorganism.

The attenuation of isopropyl malate dehydrogenase can also be achieved, inter alia, by amino acid exchanges, such as for example, by exchange of L-glycine for L-aspartate, L-asparagine or L-glutamate at position 131 of the enzyme protein.

The attenuation of isopropyl malate dehydratase can also be achieved, inter alia, by amino acid exchanges, such as, for example, by exchange of L-arginine for L-serine at position 451 or L-glycine for L-aspartate at position 456 of the enzyme protein or a combination thereof.

The attenuation of homoserine dehydrogenase can also be achieved, inter alia, by amino acid exchanges, such as, for example, by exchange of L-asparagine for L-threonine or L-serine at position 118 or L-leucine for L-proline at position 160 of the enzyme protein or a combination thereof.

The attenuation of phosphofructokinase can also be achieved, inter alia, by amino acid exchanges, such as, for example, by exchange of L-leucine for L-alanine, L-glycine or L-proline at position 109 of the enzyme protein.

The invention also provides the microorganisms prepared according to the invention, and these can be cultured continuously or discontinuously in the batch process (batch culture) or in the fed batch (feed process) or repeated fed batch process (repetitive feed process) for the purpose of production of L-amino acids. A summary of known culture methods is described in the textbook by Chmiel (Bioprozesstechnik 1. Einführung in die Bioverfahrenstechnik (Gustav Fischer Verlag, Stuttgart, 1991)) or in the textbook by Storhas (Bioreaktoren und periphere Einrichtungen (Vieweg Verlag, Braunschweig/Wiesbaden, 1994)).

The culture medium to be used must meet the requirements of the particular strains in a suitable manner. Descriptions of culture media for various microorganisms are contained in the handbook "Manual of Methods for General Bacteriology" of the American Society for Bacteriology (Washington D.C., USA, 1981).

Sugars and carbohydrates, such as e.g. glucose, sucrose, lactose, fructose, maltose, molasses, starch and cellulose, oils and fats, such as, for example, soya oil, sunflower oil, groundnut oil and coconut fat, fatty acids, such as, for example, palmitic acid, stearic acid and linoleic acid, alcohols, such as, for example, glycerol and ethanol, and organic acids, such as, for example, acetic acid, can be used as the source of carbon. These substances can be used individually or as a mixture.

Organic nitrogen-containing compounds, such as peptones, yeast extract, meat extract, malt extract, corn steep liquor, soya bean flour and urea, or inorganic compounds, such as ammonium sulfate, ammonium chloride, ammonium phosphate, ammonium carbonate and ammonium nitrate, can be used as the source of nitrogen. The sources of nitrogen can be used individually or as a mixture.

Phosphoric acid, potassium dihydrogen phosphate or dipotassium hydrogen phosphate or the corresponding sodium-containing salts can be used as the source of phosphorus. The culture medium must furthermore comprise salts of metals, such as, for example, magnesium sulfate or iron sulfate, which are necessary for growth. Finally, essential growth substances, such as amino acids and vitamins, can be employed in addition to the abovementioned substances. Suitable precursors can moreover be added to the culture medium. The starting substances mentioned can be added to the culture in the form of a single batch, or can be fed in during the culture in a suitable manner.

Basic compounds, such as sodium hydroxide, potassium hydroxide, ammonia or aqueous ammonia, or acid compounds, such as phosphoric acid or sulfuric acid, can be employed in a suitable manner to control the pH of the culture. Antifoams, such as, for example, fatty acid polyglycol esters, can be employed to control the development of foam. Suitable substances having a selective action, such as, for example, antibiotics, can be added to the medium to maintain the stability of plasmids. To maintain aerobic conditions, oxygen or oxygen-containing gas mixtures, such as, for example, air, are introduced into the culture. The temperature of the culture is usually 20° C. to 45° C., and preferably 25° C. to 40° C. Culturing is continued until a maximum of the desired product has formed. This target is usually reached within 10 hours to 160 hours.

Methods for the determination of L-amino acids are known from the prior art. The analysis can thus be carried out, for example, as described by Spackman et al. (Analytical Chemistry, 30, (1958), 1190) by anion exchange chromatography with subsequent ninhydrin derivatization, or it can be carried out by reversed phase HPLC, for example as described by Lindroth et al. (Analytical Chemistry (1979) 51: 1167-1174).

The process according to the invention is used for fermentative preparation of L-lysine.

The concentration of L-lysine can optionally be adjusted to the desired value by addition of L-lysine.

The present invention is explained in more detail in the following with the aid of embodiment examples.

EXAMPLE 1

Amplification and sequencing of the DNA of the sigA allele of strain DM1547

The *Corynebacterium glutamicum* strain DM1547 was prepared by multiple, non-directed mutagenesis, selection and mutant selection from *C. glutamicum* ATCC13032. The strain is resistant to the lysine analogue S-(2-aminoethyl)-L-cysteine and methionine-sensitive.

From the strain DM1547, chromosomal DNA is isolated by the conventional methods (Eikmanns et al., Microbiology 140: 1817-1828 (1994)). With the aid of the polymerase chain reaction, a DNA section which carries the sigA gene or allele is amplified. On the basis of the sequence of the sigA gene known for *C. glutamicum* (sequence no. 2100 and sequence no. 7065 from EP1108970), the following primer oligonucleotides are chosen for the PCR:

```
sigA-1:
5' tgatcggctgaccaactcta 3'     (SEQ ID No. 8)

sigA-2:
5' aaggtctcgaatccgagaac 3'     (SEQ ID No. 9)
```

The primers shown are synthesized by MWG Biotech (Ebersberg, Germany) and the PCR reaction is carried out by the standard PCR method of Innis et al. (PCR protocols. A Guide to Methods and Applications, 1990, Academic Press). The primers allow amplification of a DNA section of approx. 1.89 kb in length, which carries the sigA allele.

The amplified DNA fragment of approx. 1.89 kb in length which carries the sigA allele of the strain DM1547, is identified by electrophoresis in a 0.8% agarose gel, isolated from the gel and purified by conventional methods (QIAquick Gel Extraction Kit, Qiagen, Hilden).

The nucleotide sequence of the amplified DNA fragment or PCR product is determined by sequencing by MWG Biotech (Ebersberg, Germany). The sequence of the PCR product is shown in SEQ ID No. 5. The sequence of the coding region is shown again in SEQ ID No. 3. The amino acid sequences of the associated sigma factor A protein resulting with the aid of the Patentin program are shown in SEQ ID No. 6 and 4.

At position 1241 of the nucleotide sequence of the coding region of the sigA allele of strain DM1547, that is to say at position 1466 of the nucleotide sequence shown in SEQ ID No. 5, is the base thymine. At the corresponding position of the wild-type gene is the base cytosine (SEQ ID No. 1).

At position 414 of the amino acid sequence of sigma factor A of strain DM1547 is the amino acid valine (SEQ ID No. 6 and 4). At the corresponding position of the wild-type protein is the amino acid alanine (SEQ ID No. 2).

The sigA allele, which contains the base thymine at position 1241 of the coding region and accordingly codes for a sigma factor A which contains the amino acid valine at position 414 of the amino acid sequence, is called the sigA_A414V allele in the following. In the designation "sigA_A414V", A represents L-alanine, V represents L-valine and 414 indicates the position of the amino acid exchange (see SEQ ID No. 2 and 4).

EXAMPLE 2

Replacement of the sigA wild-type gene of strain DSM5715 by the sigaA_A414V allele 2.1. Production of a DNA fragment which carries the region of the sigA_A414V allele on which the mutation A414V is located From the strain DM1547, chromosomal DNA is isolated by the conventional methods (Eikmanns et al., Microbiology 140: 1817-1828 (1994)). A DNA section which carries the region of the sigA_A414V allele on which the mutation A414V is located is amplified with the aid of the polymerase chain reaction. On the basis of the sequence of the sigA gene known for *C. glutamicum* (sequence no. 2100 and sequence no. 7065 from EP-A-1108790), the following primer oligonucleotides are chosen for the PCR such that the mutation A414V is located in the central region of the amplification product:

```
sigA_XL-A1:                    (SEQ ID No. 10)
5' ac gaa ttc-cga cgg cga tga ctt cgt ag 3' sigA_XL-A2:                    (SEQ ID No. 11)
5' tg gaa ttc-cgt tcc acc tcg ctc cat tc 3'
```

The primers shown are synthesized by MWG Biotech (Ebersberg, Germany) and the PCR reaction is carried out by the standard PCR method of Innis et al. (PCR protocols. A guide to methods and applications, 1990, Academic Press). The primers allow amplification of a DNA section approx. 1.69 kb in length which carries a region of the sigA_A414V allele (SEQ ID No. 7). The primers moreover contain the sequence for a cleavage site of the restriction endonuclease EcoRI, which is marked by underlining in the nucleotide sequence shown above.

The amplified DNA fragment of approx. 1.69 kb in length which carries the sigA allele of the strain DM1547 is cleaved with the restriction endonuclease EcoRI, identified by electrophoresis in a 0.8% agarose gel and then isolated from the gel and purified by conventional methods (QIAquick Gel Extraction Kit, Qiagen, Hilden).

2.2. Construction of the exchange vector pK18mobsacB_sigA_A414V

The approx. 1.68 kb long DNA fragment cleaved with the restriction endonuclease EcoRI, which contains a region of the sigA_A414V allele which carries the mutation A414V, is incorporated by means of replacement mutagenesis with the aid of the sacB system described by Schäfer et al. (Gene, 14, 69-73 (1994)) into the chromosome of the *C. glutamicum* strain DSM5715. This system enables preparation and selection of allele exchanges which take place by homologous recombination.

The mobilizable cloning vector pK18mobsacB is digested with the restriction enzyme EcoRI and the ends are dephosphorylated with alkaline phosphatase (Alkaline Phosphatase, Boehringer Mannheim, Germany). The vector prepared in this way is mixed with the sigA_A414V fragment of approx. 1.68 kb and the mixture is treated with T4 DNA ligase (Amersham-Pharmacia, Freiburg, Germany).

The *E. coli* strain S17-1 (Simon et al., Bio/Technologie [Bio/Technology] 1:784-791, 1993) is then transformed with the ligation batch (Hanahan, In. DNA cloning. A practical approach. Vol.1. ILR-Press, Cold Spring Harbor, N.Y., 1989). Selection of plasmid-carrying cells is made by plating out the transformation batch on LB agar (Sambrook et al., Molecular Cloning: a laboratory manual. 2$^{nd}$ Ed. Cold Spring Harbor, N.Y., 1989), which was supplemented with 25 mg/l kanamycin.

Plasmid DNA is isolated from a transformant with the aid of the QIAprep Spin Miniprep Kit from Qiagen and checked by restriction cleavage with the enzyme BamHI and subsequent agarose gel electrophoresis. The plasmid is called pK18mobsacB_sigA_A414V and is shown in FIG. 1.

2.3 Allele exchange

The vector pK18mobsacB_sigA_A414V mentioned in example 2.2 is transferred by conjugation by a protocol of Schäfer et al. (Journal of Microbiology 172: 1663-1666 (1990)) into the *C. glutamicum* strain DSM5715. The vector cannot replicate independently in DSM5715 and is retained in the cell only if it is present integrated in the chromosome as the consequence of a recombination event. Selection of transconjugants, i.e. clones with integrated pK18mobsacB_sigA_A414B, is made by plating out the conjugation batch on LB agar (Sambrook et al., Molecular Cloning: a laboratory manual. 2$^{nd}$ Ed., Cold Spring Harbor, N.Y., 1989), which is supplemented with 15 mg/l kanamycin and 50 mg/l nalidixic acid. Kanamycin-resistant transconjugants are plated out on LB agar plates with 25 mg/l kanamycin and incubated for 24 hours at 33° C. For selection of mutants in which excision of the plasmid has taken place as a consequence of a second recombination event, the clones are cultured unselectively for 30 hours in LB liquid medium and then plated out on LB agar with 10% sucrose and incubated for 16 hours.

The plasmid pK18mobsacB_sigA_A414V, like the starting plasmid pK18mobsacB, contains, in addition to the kanamycin resistance gene, a copy of the sacB gene which codes for levan sucrase from *Bacillus subtilis*. The expression which can be induced by sucrose leads to the formation of levan sucrase, which catalyses the synthesis of the product levan, which is toxic to *C. glutamicum*. Only those clones in which the integrated pK18mobsacB_sigA_A414V has excised as the consequence of a second recombination event therefore grow on LB agar. Depending on the position of the second recombination event with respect to the mutation site, allele exchange or incorporation of the mutation takes place with the excision, or the original copy remains in the chromosome of the host.

Approximately 40 to 50 colonies are tested for the phenotype "growth in the presence of sucrose" and "non-growth in the presence of kanamycin". In 4 colonies which show the phenotype "growth in the presence of sucrose" and "non-growth in the presence of kanamycin", a region of the sigA gene spanning the mutation A414V is sequenced, starting from the sequencing primer sA_1 (SEQ ID No. 12), by GATC Biotech AG (Constance, Germany) to demonstrate that the mutation of the sigA_A414V allele is present in the chromosome. The primer sA_1 used is synthesized for this by GATC:

```
sA_1:
5' aag ttc tcc acc tac gca ac 3'   (SEQ ID No. 12)
```

A clone which contains the base thymine at position 1241 of the sigA gene and thus has the sigA_A414V allele was identified in this manner. This clone was called strain DSM5715sigA_A414V.

EXAMPLE 3

Preparation of Lysine

The *C. glutamicum* strain DSM5715sigaA_A414V obtained in example 2 is cultured in a nutrient medium suitable for the production of lysine and the lysine content in the culture supernatant is determined.

For this, the strain is first incubated on an agar plate for 24 hours at 33° C. Starting from this agar plate culture, a preculture is seeded (10 ml medium in a 100 ml conical flask). The medium MM is used as the medium for the preculture. The preculture is incubated for 24 hours at 33° C. at 240 rpm on a shaking machine. A main culture is seeded from this preculture such that the initial OD (660 nm) of the main culture is 0.1. The Medium MM is also used for the main culture.

| Medium MM | |
|---|---|
| CSL | 5 g/l |
| MOPS | 20 g/l |
| Glucose (autoclaved separately) | 50 g/l |
| Salts: | |
| $(NH_4)_2SO_4$ | 25 g/l |
| $KH_2PO_4$ | 0.1 g/l |
| $MgSO_4*7\ H_2O$ | 1.0 g/l |
| $CaCl_2*2\ H_2O$ | 10 mg/l |
| $FeSO_4*7\ H_2O$ | 10 mg/l |
| $MnSO_4*H_2O$ | 5.0 mg/l |
| Biotin (sterile-filtered) | 0.3 mg/l |
| Thiamine*HCl (sterile-filtered) | 0.2 mg/l |
| L-Leucine (sterile-filtered) | 0.1 g/l |
| $CaCO_3$ | 25 g/l |

The CSL (corn steep liquor), MOPS (morpholinopropanesulfonic acid) and the salt solution are brought to pH 7 with aqueous ammonia and autoclaved. The sterile substrate and vitamin solutions, as well as the $CaCO_3$ autoclaved in the dry state, are then added.

Culturing is carried out in a 10 ml volume in a 100 ml conical flask with baffles. Culturing is carried out at 33° C. and 80% atmospheric humidity.

After 72 hours, the OD is determined at a measurement wavelength of 660 nm with a Biomek 1000 (Beckmann Instruments GmbH, Munich). The amount of lysine formed is determined with an amino acid analyzer from Eppendorf-BioTronik (Hamburg, Germany) by ion exchange chromatography and post-column derivatization with ninhydrin detection.

The result of the experiment is shown in table 1.

TABLE 1

| Strain | OD (660 nm) | Lysine HCl g/l |
|---|---|---|
| DSM5715 | 8.2 | 13.57 |
| DSM5715sigA_A414V | 8.0 | 15.21 |

BRIEF DESCRIPTION OF THE FIGURE

FIG. 1: Map of the plasmid:pK18mobsacB_sigA_A414V.

The abbreviations and designations used have the following meaning. The base pair numbers stated are approximate values obtained in the context of reproducibility of measurements.

| Kan: | Kanamycin resistance gene |
|---|---|
| EcoRI: | Cleavage site of the restriction enzyme EcoRI |
| BamHI: | Cleavage site of the restriction enzyme BamHI |
| sigA: | Cloned DNA fragment containing a 3' terminal region of the sigA allele (= sigA_A414V allele) and the downstream region |
| sacB: | sacB gene |
| RP4-mob: | mob region with the replication origin for the transfer (oriT) |
| oriV: | Replication origin V |

What is claimed is:

1. An isolated protein comprising the amino acid sequence of SEQ ID NO:2 and wherein:
   a) the amino acid at position 414 of said protein is L-valine; and
   b) said protein has sigma factor A biological activity.

2. The protein of claim 1, wherein said amino acid sequence consists of the amino acid sequence of SEQ ID NO:2 but wherein the amino acid at position 414 is L-valine.

3. An isolated nucleic acid comprising a nucleotide sequence coding for the protein of either claim 1 or claim 2.

4. The isolated nucleic acid 3 wherein said isolated nucleic acid comprises the nucleotide sequence of SEQ ID NO:3.

5. A vector comprising the nucleotide sequence of the isolated nucleic acid of claim 3.

6. A coryneform bacteria transformed with the vector of claim 5.

7. A process for the production of L-lysine or of a feed additive containing L-lysine, comprising:
   a) fermenting the coryneform bacteria of claim 6 under conditions suitable for the production of L-lysine wherein said fermenting produces a fermentation liquor, and
   b) isolating said L-lysine or the fermentation liquor containing said L-lysine.

8. The process of claim 7, wherein at least one gene of the biosynthesis pathway of L-lysine is additionally overexpressed in said coryneform bacteria.

9. The process of claim 7, wherein the activity of at least one metabolic pathway that reduces the formation of L-lysine is attenuated in said coryneform bacteria.

10. The process of claim 7, wherein said composition of L-lysine or said fermentation liquor comprises >0 to 100% of the constituents of said fermentation liquor and/or of the biomass present during fermentation.

11. An isolated nucleic acid consisting of a nucleotide sequence coding for the protein of either claim 1 or claim 2.

12. The isolated nucleic acid of claim 11, wherein said isolated nucleic acid consists of the nucleotide sequence of SEQ ID NO:3.

13. A vector comprising the nucleotide sequence of the isolated nucleic acid of claim 11.

14. A coryneform bacteria transformed with the vector of claim 13.

15. A process for the production of L-lysine or of a feed additive containing L-lysine, comprising:
   a) fermenting the coryneform bacteria of claim 14 under conditions suitable for the production of L-lysine, wherein said fermenting produces a fermentation liquor, and
   b) isolating said L-lysine or the fermentation liquor containing said L-lysine.

16. The process of claim 15, wherein at least one gene of the biosynthesis pathway of L-lysine is additionally overexpressed in said coryneform bacteria.

17. The process of claim 15, wherein the activity of at least one metabolic pathway that reduces the formation of L-lysine is attenuated in said coryneform bacteria.

* * * * *